United States Patent
Cong et al.

(10) Patent No.: US 11,278,202 B2
(45) Date of Patent: Mar. 22, 2022

(54) SYSTEMS AND METHODS FOR VIBRATION-BASED COMMUNICATION

(71) Applicant: Verily Life Sciences LLC, South San Francisco, CA (US)

(72) Inventors: Peng Cong, Burlingame, CA (US); You Zou, Redwood City, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/226,823

(22) Filed: Dec. 20, 2018

(65) Prior Publication Data

US 2019/0191996 A1   Jun. 27, 2019

Related U.S. Application Data

(60) Provisional application No. 62/608,956, filed on Dec. 21, 2017.

(51) Int. Cl.
| | |
|---|---|
| *A61B 5/00* | (2006.01) |
| *G16H 40/63* | (2018.01) |
| *A61B 5/145* | (2006.01) |
| *A61B 5/024* | (2006.01) |
| *A61B 5/318* | (2021.01) |

(52) U.S. Cl.
CPC .......... *A61B 5/0015* (2013.01); *A61B 5/0031* (2013.01); *G16H 40/63* (2018.01); *A61B 5/02444* (2013.01); *A61B 5/14532* (2013.01); *A61B 5/318* (2021.01)

(58) Field of Classification Search
CPC . A61B 5/0015; A61B 5/0031; A61B 5/02444; A61B 5/0402; A61B 5/14532; G16H 40/63

USPC .......................................................... 600/301
See application file for complete search history.

(56) References Cited

U.S. PATENT DOCUMENTS

| | | | |
|---|---|---|---|
| 6,850,782 B2 | 2/2005 | Bright et al. | |
| 2011/0053577 A1 | 3/2011 | Lee et al. | |
| 2011/0169622 A1 | 7/2011 | Billmaier et al. | |
| 2016/0310077 A1* | 10/2016 | Hunter | .................. A61B 5/686 |
| 2018/0043168 A1* | 2/2018 | Kim | .................... H04W 12/001 |

FOREIGN PATENT DOCUMENTS

| | | |
|---|---|---|
| CA | 2553507 | 11/2009 |
| CN | 102484664 | 5/2012 |
| WO | 2016133813 | 8/2016 |

OTHER PUBLICATIONS

Roy et al. "Ripple II: Faster Communication through Physical Vibration", Proceedings of the 13th USENIX Symposium on Networked Systems Design and Implementation, Mar. 2016, pp. 671-684. (Year: 2016).*

(Continued)

*Primary Examiner* — Erin M Pataleski
(74) *Attorney, Agent, or Firm* — Kilpatrick Townsend & Stockton LLP

(57) ABSTRACT

Systems and methods for vibration-based communication disclosed. In one embodiment, a system includes: a motion sensor configured to detect vibrations from a remote device; a processor coupled to the motion sensor and configured to: receive signals from the motion sensor; and activate a network connection based on signals from the motion sensor.

23 Claims, 3 Drawing Sheets

(56) References Cited

OTHER PUBLICATIONS

International Application No. PCT/US2018/066644, "International Search Report and Written Opinion", dated Mar. 13, 2019, 12 pages.
Younghyun et al., "Vibration-based Secure Side Channel For Medical Devices", 52nd ACM//EDAC/IEEE Design Automation Conference (DAC), IEEE, Jun. 8, 2015, pp. 1-6.

* cited by examiner

SYSTEMS AND METHODS FOR VIBRATION-BASED COMMUNICATION

CROSS-REFERENCE TO RELATED APPLICATIONS

This application claims the benefit of Provisional Application No. 62/608,956, filed on Dec. 21, 2017 and entitled "Systems and Methods for Vibration-Based Communication" the entirety of which is hereby incorporated herein by reference.

BACKGROUND

Some biometric sensors may be implanted in human tissue. Implanting a biometric sensor may provide for more accurate and substantially continuous monitoring. However, once a biometric sensor is implanted in human tissue, its battery cannot be easily replaced. Thus extending battery life may be of high importance in implantable devices.

SUMMARY

In one embodiment, a system of the present disclosure may comprise: a motion sensor configured to detect vibrations from a remote device; a processor coupled to the motion sensor and configured to: receive signals from the motion sensor; and activate a network connection based on signals from the motion sensor.

In another embodiment, a system of the present disclosure may comprise: a processor configured to: control an actuator configured to output a vibration configured to be received by a device embedded in human tissue; and a network interface configured to receive data from the device embedded in human tissue.

In another embodiment, a method according to the present disclosure may comprise: receiving signals from a motion sensor configured to detect vibrations from a remote device, the motion sensor coupled within a device embedded in human tissue; and activating a network connection based on signals from the motion sensor.

In another embodiment, a method according to the present disclosure may comprise: controlling an actuator configured to output a vibration configured to be received by a device embedded in human tissue; and receiving data from the device embedded in human tissue.

Another embodiment of the present disclosure may comprise a computer readable medium comprising program code configured, when executed by a processor, to cause the processor to: receive signals from a motion sensor configured to detect vibrations from a remote device wherein the motion sensor is disposed within a housing configured to be embedded in human tissue; and activate a network connection based on signals from the motion sensor.

Another embodiment of the present disclosure may comprise a computer readable medium comprising program code configured, when executed by a processor, to cause the processor to: control an actuator configured to output a vibration configured to be received by a device embedded in human tissue; and receive data from the device embedded in human tissue.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

DETAILED DESCRIPTION

Figure 1:
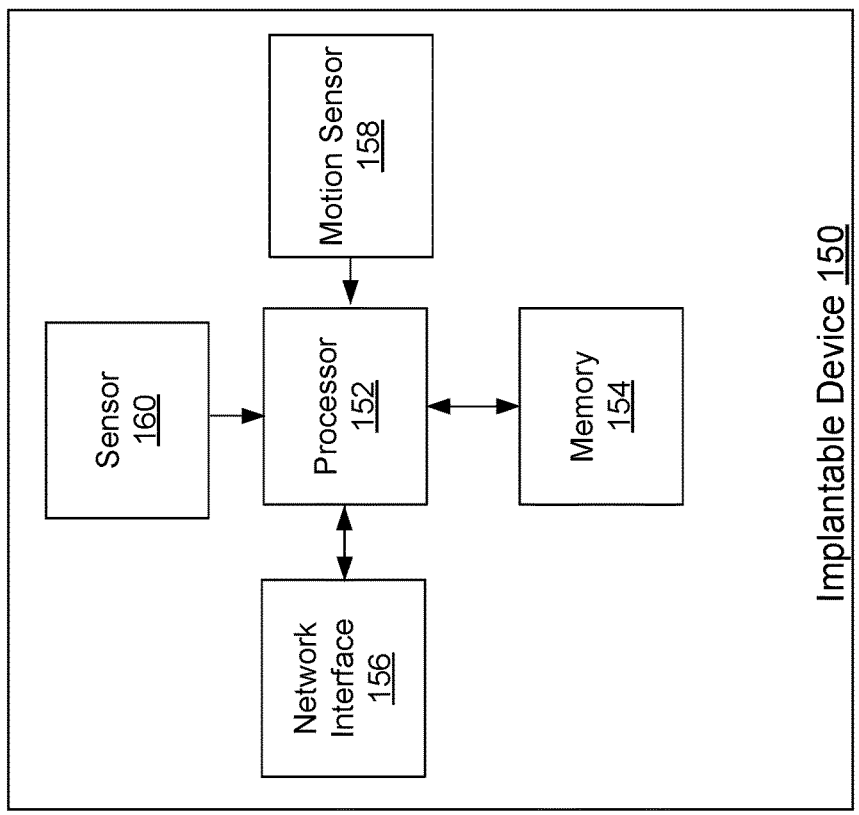
FIG. 1 shows an illustrative system for vibration-based communication according to one embodiment.
Figure 1:
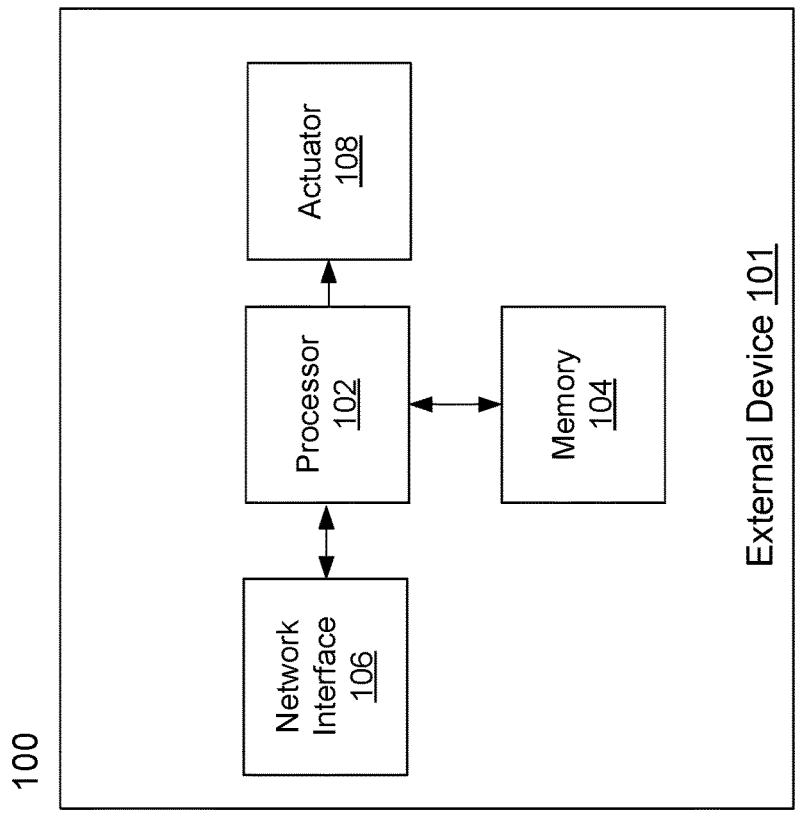

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of Vibration-Based Communication

One illustrative embodiment of the present disclosure comprises a biometric sensor (e.g., an Electrocardiogram (EKG), Electroencephalograph (EEG), Magnetoencephalograph (MEG), or analyte sensor, etc.) that is configured to be embedded in human tissue (the "embedded sensor" or the "implanted sensor"). For example, such an embedded sensor may be surgically implanted in human tissue. The embedded sensor is configured to store monitored data and periodically transmit that data to a remote device.

In the illustrative embodiment, the embedded sensor may comprise a motion sensor (e.g., an accelerometer) configured to detect vibrations. When the motion sensor detects vibrations it may activate functionality within the embedded sensor. For example, in one embodiment, vibrations may be used to activate data transmission functionality in the embedded sensor. Thus, when the motion sensor detects vibrations, it may transmit a signal to a processor that activates a network interface, e.g., a Bluetooth or Bluetooth Low Energy (BLE) network interface that transmits data to a remote device.

In the illustrative embodiment, vibrations are received from a device placed on the surface of the skin of the person in whom the embedded sensor is implanted. In the illustrative embodiment the device comprises a handheld mobile device, e.g., a smartphone. The smartphone may comprise one or more actuators configured to output haptic effects. The mobile device may use these actuators to output vibrations, which, when the mobile device is placed on or near the skin surface, may be detected by a motion sensor of the embedded sensor.

Further, in some embodiments, the motion sensor may be configured to detect more complex vibrations. For example, in some embodiments, data may be encoded in vibrations output by an actuator of the mobile device. For example, control data for the embedded sensor may be encoded in vibrations through Frequency Modulation (FM), Amplitude Modulation (AM), Pulse-Width Modulation (PWM) or any other type of encoding. This encoded data may be transmitted via vibration to a motion sensor of the embedded sensor. The motion sensor detects these vibrations and transmits signals associated with the vibrations to a processor, which interprets the encoded data and may control the embedded sensor based on the encoded data.

In one illustrative embodiment, an external device (e.g., a smartphone) may output a vibration to the surface of the user's skin. The vibration comprises data associated with activating and pairing a Bluetooth or Bluetooth Low Energy (BLE) network interface on the embedded device with the smartphone. When an accelerometer in the embedded device receives the vibration it outputs electrical signals associated with the vibration. A processor on the embedded device decodes these signals and controls the network interface based on the data encoded in the vibration. Once the network interface is paired, the embedded device may transmit data to the smartphone or receive data from the smartphone. For example, in one embodiment, the embedded device may transmit stored biometric data monitored from one or more internal sensors. The illustrative embodiment may conserve energy, because a network interface of the embedded device can be inactive until a recipient device (e.g., the smartphone that output vibrations) is available to receive transmitted data.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Illustrative Systems for Vibration Based Communication

FIG. 1 shows an illustrative system 100 for vibration-based communication. As shown in FIG. 1 the system comprises an external device 101 and an implantable device 150. In the embodiment shown in FIG. 1, the external device 101 may comprise a device external to the body, e.g., a mobile device (smartphone, tablet, laptop, or other handheld device) or a dedicated medical interface device. The external device 101 may comprise one or more additional components, e.g., sensors, cameras, or input/output devices, such as buttons, displays, touch-screens, etc.

In the embodiment shown in FIG. 1, the external device 101 comprises a processor 102, memory 104, a network interface 106, and an actuator 108. The processor 102 is electrically coupled to memory 104, which comprises processor executable instructions configured to cause the processor to perform operations described herein. The memory 104 can comprise any suitable tangible (and non-transitory) computer-readable medium such as RAM, ROM, EEPROM, or the like, and embodies program components that configure operation of the external device 101. Memory 104 may also be configured to store data received from processor 102 or network interface 106.

Processor 102 is further coupled to a network interface 106 configured to transmit and receive data. The network interface 106 may represent one or more of any components that facilitate a network connection. Examples include, but are not limited to, wired interfaces such as Ethernet, USB, IEEE 1394, and/or wireless interfaces such as IEEE 802.11, Bluetooth, Bluetooth Low Energy (BLE), or radio interfaces for accessing cellular telephone networks (e.g., transceiver/antenna for accessing a CDMA, GSM, UMTS, or other mobile communications network).

Processor 102 is further coupled to an actuator 108. Actuator 108 represents one or more components configured to receive signals and output vibrations. In some embodiments these vibrations may comprise a frequency range from 50-500 Hz or higher. Processor 102 may encode information in these vibrations, e.g., through Frequency Modulation (FM), Amplitude Modulation (AM), Pulse-Width Modulation (PWM) or any other type of encoding, and this encoded information may be used to control one or more functions of implantable device 150. In some embodiments, actuator 108 may comprise one or more of a piezoelectric actuator, an electric motor, an electro-magnetic actuator, a voice coil, a shape memory alloy, an electroactive polymer, a solenoid, an eccentric rotating mass motor (ERM), or a linear resonant actuator (LRA).

As shown in FIG. 1, the implantable device 150 comprises a sensor implanted in the body of a person. The implantable device 150 comprises a processor 152, memory 154, network interface 156, motion sensor 158, and a sensor 160. The processor 152 is electrically coupled to memory 154, which comprises processor executable instructions configured to cause the processor to perform operations described herein. The memory 154 can comprise any suitable tangible (and non-transitory) computer-readable medium such as RAM, ROM, EEPROM, or the like, and embodies program components that configure operation of the implantable device 150. Memory 154 may also be configured to store data received from processor 152 or network interface 156.

Processor 152 of the implantable device 150 is further coupled to a network interface 106 configured to transmit and receive data. The network interface 156 may represent one or more of any components that facilitate a network connection. Examples include, but are not limited to, wired interfaces such as Ethernet, USB, IEEE 1394, and/or wireless interfaces such as IEEE 802.11, Bluetooth, Bluetooth Low Energy (BLE), or radio interfaces for accessing cellular telephone networks (e.g., transceiver/antenna for accessing a CDMA, GSM, UMTS, or other mobile communications network).

Processor 152 of the implantable device is further in communication with a motion sensor 158, which is configured to detect vibrations, e.g., vibrations received from actuator 108 of external device 101. For example, motion sensor 158 may comprise one or more of e.g., an accelerometer (e.g., one or more of micro electro-mechanical systems (MEMS), piezoelectric, piezoresistive, and/or capacitive components that convert mechanical motion into an electrical signal), gyroscope, GPS, or other sensor(s) configured to detect movement or vibrations and output electrical signals associated with the movement or vibration to the processor.

Processor 152 is further in communication with a sensor 160, which is configured to monitor one or more features associated with the person in which the implantable device 150 has been implanted. For example, sensor 160 may comprise one or more of e.g., an Electrocardiogram (EKG), Electroencephalography (EEG), Magnetoencephalography (MEG), or analyte sensor. Processor 152 is configured to receive signals from the sensor 160 and store these signals in memory 154 or transmit these signals to external device 101 via network interface 156.

Figure 2:
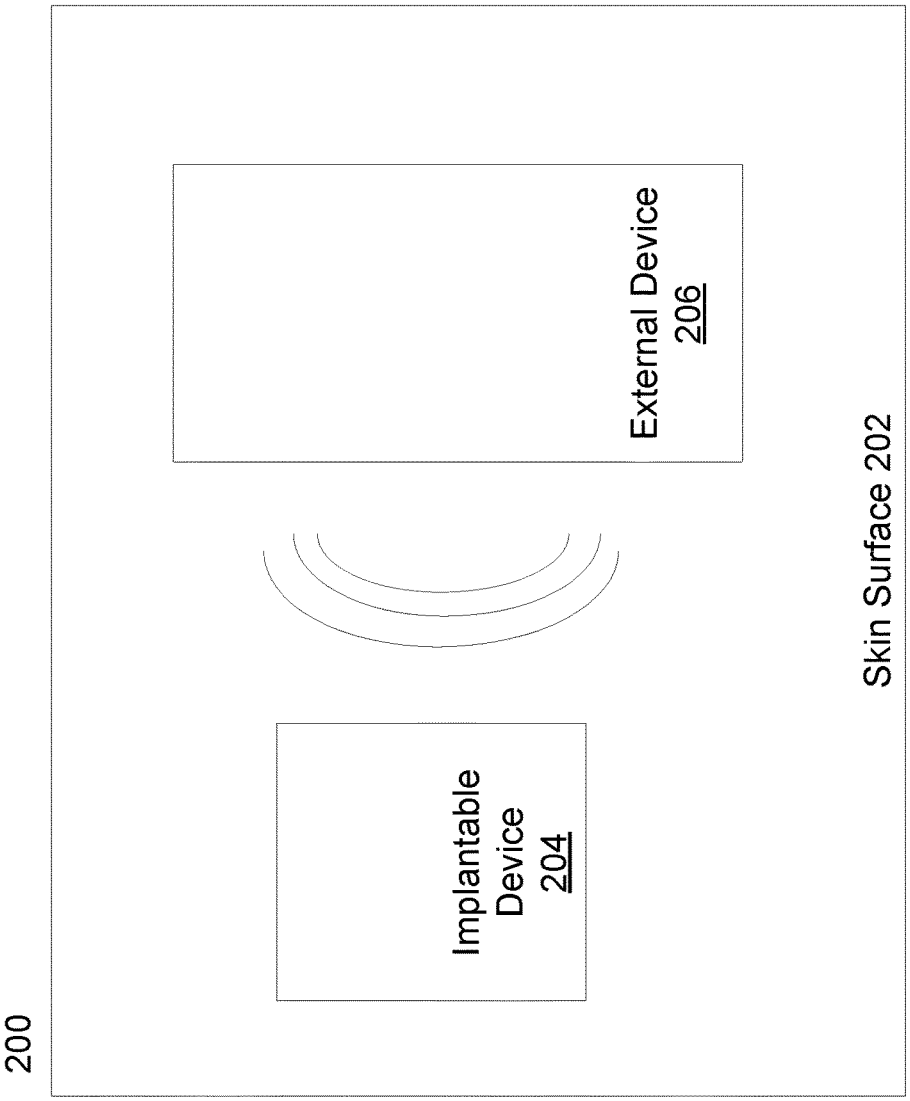
FIG. 2 shows an illustrative system for vibration-based communication according to one embodiment.

Turning now to FIG. 2, FIG. 2 shows an illustrative system 200 for vibration-based communication. As shown in FIG. 2, the system 200 comprises an implantable device 204 (similar to implantable device 150 described above) and an external device 206 (similar to external device 101 described above. As is shown in FIG. 2, the implantable device 204 is embedded in human tissue. For example, in one embodiment, the implantable device 204 may be surgically embedded in human tissue. Further, as shown in FIG. 2, the external device 206 is in communication with implantable device 204 via vibrations. These vibrations are output onto or near the skin surface 202 and vibrate the tissue between the implantable device 204 and the skin surface 202. Data encoded in vibrations may enable external device 206 to transmit information or control signals to implantable device 204. For example, in one embodiment, external device 206 may send a control signal via vibrations to implantable device 204, which causes implantable device 204 to activate an internal sensor. In another embodiment, external device 206 may send a control signal via vibrations to implantable device 204, which causes implantable device 204 to transmit data to, or receive data from, external device 206 via Bluetooth or BLE.

Illustrative Methods for Vibration-Based Communication

Figure 3:
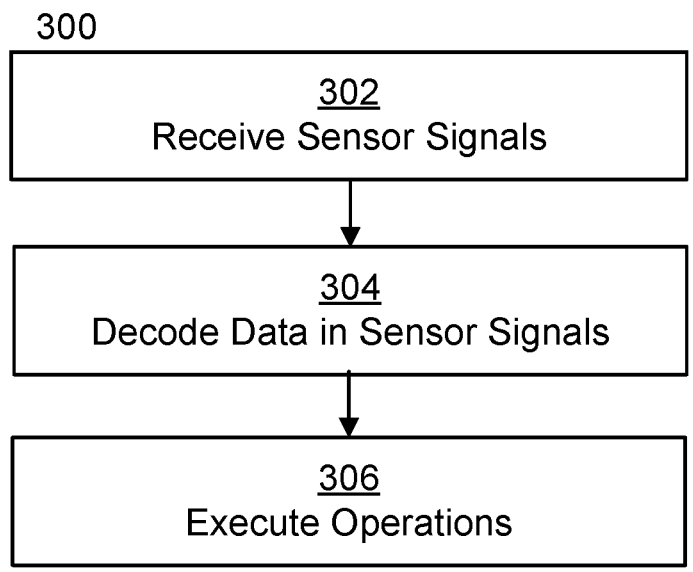
FIG. 3 shows a flow chart for an illustrative method for vibration-based communication according to one embodiment.

FIG. 3 shows a flow chart for an illustrative method for vibration-based communication according to one embodiment. In some embodiments, the steps in FIG. 3 may be performed in a different order. Alternatively, in some embodiments, one or more of the steps shown in FIG. 3 may be skipped, or additional steps not shown in FIG. 3 may be performed. The steps below are described with reference to components described above with regard to system 100 shown in FIG. 1.

The method 300 begins at step 302 when processor 152 receives sensor signals from motion sensor 158. These sensor signals are electrical signals output by motion sensor 158, and which are representative of vibrations received from actuator 108 of an external device 101.

Next at step 304 the processor 152 decodes data stored in sensor signals. In some embodiments, the vibrations comprise encoded information configured to control processor 152 to execute certain operations (e.g., transmit data, measure data, provide system information, etc.). In other embodiments, these vibrations do not contain encoded information and instead trigger the processor 152 to activate or deactivate one or more components.

Then, at step 306, the processor 152 executes operations based on the encoded data. For example, in one embodiment, data encoded in the vibrations may instruct the processor 152 to activate network interface 156 and transmit data stored in memory 154 to a remote device, such as external device 101. In another embodiment, the vibrations may contain encoded data configured to cause the processor 152 to activate or deactivate sensor 160. Further, in one embodiment, the encoded data may be configured to cause processor 152 to pair with a network interface 156 of external device 101 to send data to or receive data from the external device 101.

In one embodiment, the actuator 108 may output a vibration that contains encoded data needed for pairing a Bluetooth connection between network interface 106 and network interface 156. In such an embodiment, the processor 152 may use the data encoded in the vibrations to activate a Bluetooth network connection and pair the Bluetooth network connection to external device 101 without additional user input. In yet another embodiment, the encoded data may comprise updated operating information associated with implantable device 150, e.g., the encoded data may comprise a software or firmware update for the implantable device 150. Processor 152 may receive this encoded information and update the software or firmware for the implantable device 150.

Figure 4:
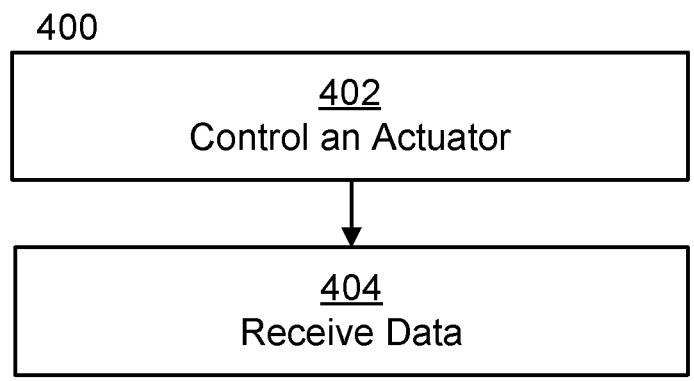
FIG. 4 shows a flow chart for an illustrative method for vibration-based communication according to one embodiment.

FIG. 4 shows a flow chart for an illustrative method for vibration-based communication according to one embodiment. In some embodiments, the steps in FIG. 4 may be performed in a different order. Alternatively, in some embodiments, one or more of the steps shown in FIG. 4 may be skipped, or additional steps not shown in FIG. 4 may be performed. The steps below are described with reference to components described above with regard to system 100 shown in FIG. 1.

The method 400 begins at step 402 when processor controls the actuator 108 to output vibrations. In some embodiments, the vibrations may comprise encoded information, e.g., information encoded through Frequency Modulation (FM), Amplitude Modulation (AM), Pulse-Width Modulation (PWM) or any other type of encoding. This information may comprise instructions configured to cause a processor 152 of the implantable device 150 to execute operations, e.g., to cause it to transmit data, activate a network interface 156 to receive data or to pair with external device 101, e.g., via Bluetooth or BLE.

Next, at step 404, the processor 102 receives data via network interface 106. The data may comprise data measured by sensor 160 and stored on memory 154 of the implantable device 150. This data may transmitted via network interface 156, which to conserve energy is activated only after motion sensor 158 receives vibration information from actuator 108.

Advantages of Vibration-Based Communication

There are numerous advantages of vibration-based communication. For example, embodiments of the present disclosure preserve the battery life of implanted devices because power consuming circuitry on the sensor may remain inactive until a vibration is received. This may preserve battery life by keeping components inactive longer. This may add value to these devices be enabling them to be used for longer periods of time. Further, once the device is implanted, its battery life may become an issue because the battery may not be able to be replaced or recharged easily.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. Processors used to implement methods described herein may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed is:

1. A system embedded in human tissue comprising:
   a motion sensor configured to detect vibrations from a remote device;
   a processor coupled to the motion sensor and configured to:
      receive signals from the motion sensor;
      decode data encoded in the vibrations using Frequency Modulation, wherein the data comprises operating information comprising a firmware update, wherein the vibrations are configured to transmit data at a data transfer rate sufficient to transmit the firmware update; and
      activate a network connection based on one or more of the signals from the motion sensor.

2. The system of claim 1, wherein the remote device comprises a smartphone.

3. The system of claim 1, wherein the network connection comprises one or more of: Bluetooth, Bluetooth Low Energy (BLE), Near Field Communication (NFC), or Wi-Fi.

4. The system of claim 1, wherein the vibrations comprise encoded data and wherein the processor is configured to control the network connection to transmit stored data based on the encoded data.

5. The system of claim 1, further comprising a sensor configured to monitor one or more of: heartrate, blood pressure, blood sugar, or brain activity.

6. A system comprising:
   a processor configured to:
   control an actuator configured to output a vibration configured to be received by a device embedded in human tissue to activate a network connection in the device embedded in human tissue, the vibration comprising data encoded using Frequency Modulation, the encoded data comprising operating information comprising a software update, wherein the vibrations are configured to transmit data at a data transfer rate sufficient to transmit the software update; and a network interface configured to receive data from the device embedded in human tissue.

7. The system of claim 6, wherein the system is a smartphone.

8. The system of claim 6, wherein the network interface comprises one or more of: Bluetooth, Bluetooth Low Energy (BLE), Near Field Communication (NFC), or Wi-Fi.

9. The system of claim 6, wherein the vibration comprises encoded data and wherein the processor is configured to control the network interface to transmit stored data based on the encoded data.

10. The system of claim 6, wherein the vibration comprises encoded instructions to activate the device embedded in human tissue.

11. A method comprising:
receiving signals from a motion sensor configured to detect vibrations from a remote device, the motion sensor coupled within a device embedded in human tissue;
decoding data encoded in the vibrations using Frequency Modulation, wherein the data comprises operating information, wherein the vibrations are configured to transmit data at a data transfer rate sufficient to transmit the operating information; and
activating a network connection based on one or more of the signals from the motion sensor.

12. The method of claim 11, wherein the remote device comprises a smartphone.

13. The method of claim 11, wherein the network connection comprises one or more of: Bluetooth, Bluetooth Low Energy (BLE), Near Field Communication (NFC), or Wi-Fi.

14. The method of claim 11, wherein the vibrations comprise encoded data and further comprising controlling the network connection to transmit stored data based on the encoded data.

15. A method comprising:
controlling an actuator configured to output a vibration configured to be received by a device embedded in human tissue to activate a network connection in the device embedded in human tissue, the vibration comprising data encoded using Frequency Modulation, the data comprising operating information comprising instructions to cause the device embedded in human tissue to transmit data, wherein the vibrations are configured to transmit data at a data transfer rate sufficient to transmit the operating information; and
receiving data from the device embedded in human tissue.

16. The method of claim 15, wherein the data is received by a smartphone.

17. The method of claim 15, wherein data from the device is received using a network connection comprising one or more of: Bluetooth, Bluetooth Low Energy (BLE), Near Field Communication (NFC), or Wi-Fi.

18. The method of claim 15, wherein the vibration comprises encoded data configured to cause the device embedded in human tissue to transmit stored data based on the encoded data.

19. A non-transitory computer-readable medium comprising program code, which when executed by a processor, is configured to cause the processor to:
control an actuator configured to output a vibration configured to be received by a device embedded in human tissue to activate a network connection in the device embedded in human tissue, wherein the vibrations are configured to transmit data at a data transfer rate sufficient to transmit operating information;
decode data encoded in the vibrations using Frequency Modulation, wherein the data comprises the operating information, the operating information comprising instructions to cause the device embedded in human tissue to activate a network interface to receive data; and
receive data from the device embedded in human tissue.

20. The non-transitory computer-readable medium of claim 19, wherein the data is received by a smartphone.

21. The non-transitory computer-readable medium of claim 19, wherein the data from the device embedded in human tissue is received using a network connection comprising one or more of: Bluetooth, Bluetooth Low Energy (BLE), Near Field Communication (NFC), or Wi-Fi.

22. The non-transitory computer-readable medium of claim 19, wherein the vibration comprises encoded data configured to cause the device embedded in human tissue to transmit stored data based on the encoded data.

23. The system of claim 1, wherein the data comprises operating information comprising instructions to cause the device embedded in human tissue to activate a network interface to pair with the remote device.

* * * * *